United States Patent [19]

Morrow

[11] 3,959,087
[45] May 25, 1976

[54] IN-LINE RESIDUAL CHLORINE ANALYZER
[75] Inventor: James J. Morrow, Norristown, Pa.
[73] Assignee: Fischer & Porter Co., Warminster, Pa.
[22] Filed: Apr. 17, 1974
[21] Appl. No.: 461,810

Related U.S. Application Data
[63] Continuation of Ser. No. 855,619, Sept. 5, 1969, abandoned.

[52] U.S. Cl. .............................. 204/1 T; 204/195 R
[51] Int. Cl.² ......................................... G01N 27/46
[58] Field of Search ........................... 204/195, 1 T

[56] References Cited
UNITED STATES PATENTS

| | | | |
|---|---|---|---|
| 2,350,378 | 6/1944 | Wallace | 204/195 R |
| 2,382,735 | 8/1945 | Marks | 204/195 R |
| 2,414,411 | 1/1947 | Marks | 204/195 R |
| 3,235,477 | 2/1966 | Keyser et al. | 204/195 R |
| 3,413,199 | 11/1968 | Morrow | 204/195 R |

Primary Examiner—John H. Mack
Assistant Examiner—H. A. Feeley

[57] ABSTRACT

A residual chlorine analyzer for testing chlorinated water, and including an amperometric cell whose flow passage is provided with spaced measuring and counter-electrodes both formed of copper. A sample stream diverted from the water to be tested is continuously conducted through the flow passage between the electrodes. Impressed across the electrodes is a voltage which renders the measuring electrode negative relative to the counter-electrode to an extent causing the cell to operate in a saturation voltage zone wherein the intensity of current passing through the cell is independent of changes in the impressed voltage and is proportional to the bulk concentration of the chlorine in solution. The current is measured by a meter calibrated in terms of concentration to maintain an uninterrupted, in-line check on residual chlorine in the water.

3 Claims, 3 Drawing Figures

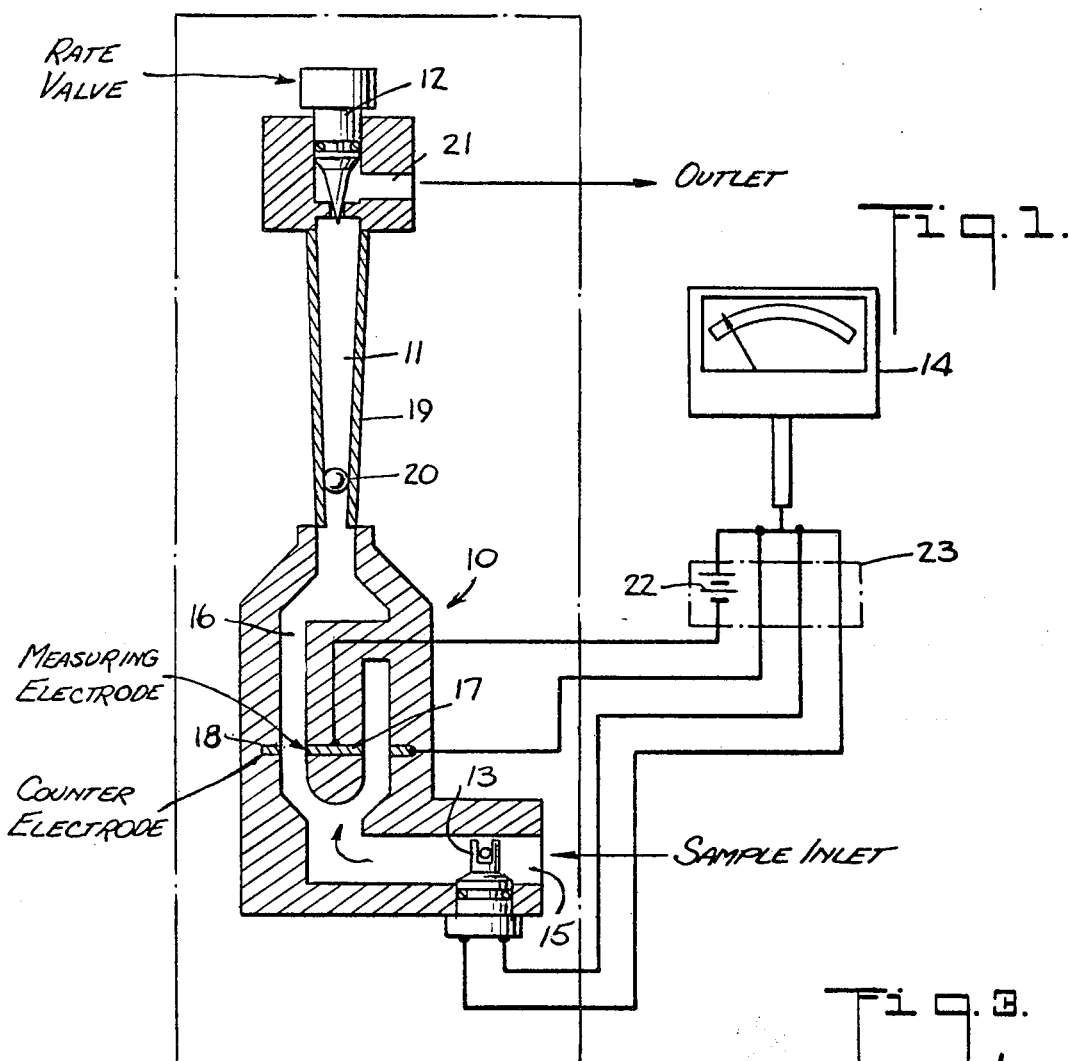
Fig. 1.
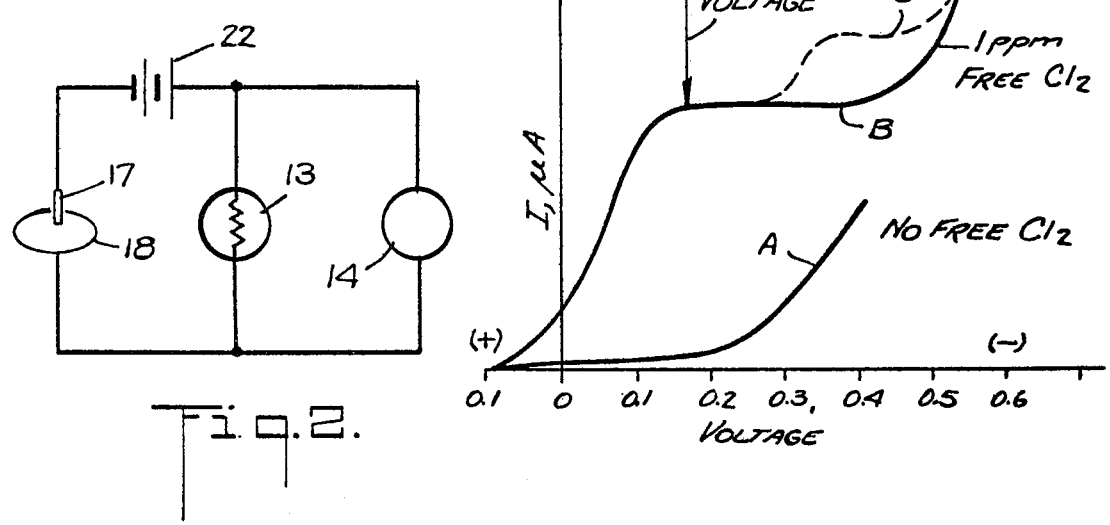
Fig. 2.
Fig. 3.

IN-LINE RESIDUAL CHLORINE ANALYZER

RELATED APPLICATION

This application is a continuation of copending application Ser. No. 855,619 filed Sept. 5, 1969 now abandoned.

BACKGROUND OF INVENTION

This invention relates generally to the measurement of chlorine residuals, and more particularly to an in-line analyzer for continuously and accurately measuring chlorine residuals without the use of reagents.

Disinfection of swimming pools is essential to health and safety, for it serves to destroy pathogens and other organisms present in water entering the pool, as well as organisms introduced by persons making use of the pool. The most acceptable method of disinfection is chlorination which involves continuously feeding either chlorine gas, calcium hypochlorite or sodium hypochlorite into the swimming water at a controlled and regulated rate in sufficient quantity to impart and to maintain a chlorine residual of specified type and quantity.

When a solution of chlorine gas or hypochlorite is added to swimming water, it reacts to form hydrochloric acid and hydrochlorous acid ($Cl_2 + H_2O \rightarrow HCl + HOCl$). The hypochlorous acid ionizes or dissociates into hydrogen and hypochlorite ions ($HOCl \rightarrow H^+ + OCl^-$). Both reactions are dependent upon the pH value of the water. The first equation predominates at low pH levels, and the second at higher levels. At low pH levels, free available chlorine residuals consist predominantly of hypochlorous acid (HOCl). Above pH 7.5, hypochlorite ions predominate, while above pH 9.5 free available chlorine residuals consist almost entirely of hypochlorite ions.

The quantity of any selected chlorination agent that must be applied is referred to as the "dosage." This dosage quantity, in turn, includes not only the quantity of the chlorination agent required to impart to the water the specified chlorine residual but also includes the quantity of chlorination agent required to satisfy the chlorine demand of the water. By convention, all three of these distinct quantities, — the demand quantity, the residual quantity and the dosage quantity, — are expressed in parts per million (ppm), i.e., parts of chlorine per million parts of water.

The chlorine demand is the ppm chlorine that is required to destroy all harmful bacteria and to react with any oxidizable organic or inorganic chemical substances present in the water. The chlorine demand value is also related to the pH of the water, the temperature of the water, and the particular type of chlorine residual desired. Since the demand is affected by bathing load and climatic conditions, experience is the only practical solution to the problem of determining the chlorine demand of a swimming water.

Chlorine residual is the ppm chlorine present in the water in a form which is either immediately available or potentially available to react with pollutants introduced into the water. Therefore chlorine residual is of two types: free available chlorine residual, the form immediately available for reaction; and combined available chlorine residual, the form potentially available for reaction.

Free available chlorine is chlorine which is present in the form of the hypochlorite ion. This ion is a constituent ion of both calcium hypochlorite and sodium hypochlorite, or is formed when chlorine gas dissolves in water. In this form, chlorine is extremely reactive. Combined available chlorine is chlorine which is present in the form of one of the chloramine compounds; any one of the series of compounds formed from the reaction between chlorine and ammonia or some nitrogenous organic compound. In this form, reactivity of chlorine is reduced considerably.

To attain effective disinfection, the free chlorine residual should not fall below 0.4 ppm. The safe upper limit is approximately 1.0 ppm. However, the exact range must be determined by experience as it will normally vary from one bathing place to another.

There is a need, therefore, in swimming pools, to monitor the free chlorine residual in the water to be sure that adequate disinfection is maintained. The most commonly used technique for this purpose is the color comparator test, in which a measured volume of the water is reacted with a measured amount of reagent, such as ortho tolidine, which changes its depth of color (yellow) to an extent depending on the concentration of free chlorine. The resultant color of the reagent is then compared with color standards to determine the concentration.

Since free available chlorine reacts immediately, the depth of the initial color produced is representative of this type of residual chlorine. On the other hand, combined available chlorine requires a longer period for reaction with the ortho tolidine. Hence a 10-second reading after the reagent is added to the sample of water affords the value for free available chlorine, while a 5-minute reading gives the value for combined available chlorine.

The difficulty with this technique is that it does not monitor the chlorine residual at all times, but only on those occasions when the pool attendant takes the trouble to carry out the test. Hence there may be periods when the free chlorine residual in the water is well below the prescribed level for proper disinfection.

To overcome these drawbacks, continuous electrochemical techniques have been developed, making use of amperometric cells, but such instruments, to be effective, require the use of buffering agents and other reagents which render the technique relatively complicated and expensive. Moreover, should the amount and concentration of reagent not be carefully controlled, the instrument reading becomes inaccurate and unreliable.

BRIEF DESCRIPTION OF INVENTION

In view of the foregoing, it is the primary object of this invention to provide a simple and reliable instrument capable of indicating residual chlorine so that the efficacy of chlorination may be measured and controlled.

More specifically, it is an object of this invention to provide an in-line analyzer for continuously and accurately measuring residual chlorine in swimming-pool water without the use of a reagent.

A significant advantage of an analyzer in accordance with the invention is that it is compensated for temperature effect, and its measurement remains accurate despite flow rate variations within a limited range. Moreover, since the analyzer provides an electrical output signal proportional to residual chlorine concentration, the signal may be transmitted to effect automatic control of the chlorination system to maintain the residual chlorine in the water at a prescribed level at all times.

Briefly stated, these objects are accomplished in an analyzer including an amperometric cell whose flow passage is provided with spaced measuring and counter-electrodes both fabricated of copper, a sample stream deverted from the swimming-pool water being continuously conducted through the flow passage between the electrodes. Impressed across the electrodes is a voltage which renders the measuring electrode negative relative to the counter-electrode and to an extent causing said cell to operate in a saturation voltage zone wherein the intensity of current passing through the cell is independent of changes of voltage and is proportional to the bulk concentration of the chlorine in solution, the current being measured by a meter calibrated in terms of concentration to maintain a running check on residual chlorine.

The output of the cell is also a function of the temperature of the sample stream, and to correct therefor, a thermistor exposed to the stream is connected in the output circuit to effect compensation providing readings independent of changes in temperature.

BRIEF DESCRIPTION OF DRAWING

For a better understanding of the invention, as well as other objects and further features thereof, reference is made to the following detailed description to be read in conjunction with the accompanying drawing, wherein:

FIG. 1 schematically illustrates a residual chlorine analyzer in accordance with the invention;

FIG. 2 is the equivalent electrical circuit of the analyzer; and

FIG. 3 is a graph illustrative of the electrical currents produced by the analyzer cell and the effect of voltage thereon.

DETAILED DESCRIPTION OF INVENTION

In a conventional amperometric cell wherein two metal electrodes are exposed to a solution containing a strong oxidizing agent, the electrodes are connected in series with a voltage source to a current-indicating meter. A cell of this type is capable of measuring the concentration of the oxidizing agent in solution when the current output of the cell is substantially proportional to concentration.

In a situation in which chlorine is the oxidizing agent in question, it is electrochemically reduced to chloride ions at the cathode of the cell by accepting electrons, whereas the anode of the cell goes into solution, thereby releasing electrons to complete the circuit.

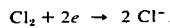

where:
Cl is chlorine
$e$ is electrons, and
M is a metal which forms a divalent ion.

The cathode of the cell may be more appropriately called the measuring electrode in that the electrochemical reaction of interest occurs at this electrode, while the cell anode is more properly called the counter-electrode.

To operate effectively in measuring residual chlorine, the measuring electrode must satisfy the following basic criteria:

A. It must be of a material that does not undergo chemical reaction with substances normally encountered in water.
B. It must present an electrochemically active surface such that electrons transfer with ease.
C. It must maintain its electroactive surface for a protracted period of time.

The requirements for the counter-electrode are less stringent, for it merely has to supply electrons at a rate dependent on the cathodic reaction. However, it too must be inert to chemical reactions with substances commonly found in swimming-pool water.

An electrochemical cell constituted by electrodes which fulfill the above requirements, can be either galvanic in nature, or of the impressed potential type. In the galvanic cell, one must use different metals for the anode and cathode to produce a potential difference therebetween sufficient to cause an electrochemical reaction. In the impressed-potential type of cell, the metal electrodes do not of themselves generate sufficient potential, and it is necessary to add a potential derived from an external source which is applied across the cell electrodes to bring about the desired electrochemical reaction.

If gold, platinum or other noble metal is used for a measuring electrode in conjunction with a copper counter-electrode, the above-noted criterion C is not met unless the pH of the solution is maintained below a value of pH 5. Inasmuch as most water supplies operate well above this pH value, one must normally add a buffering agent to the solution before it enters the measuring cell in order to maintain the electro-active surface of the measuring electrode.

It has been discovered, however, that if a measuring electrode fabricated of copper is employed in conjunction with a copper counter-electrode, and a potential is applied across these electrodes to maintain the measuring electrode at a potential which is negative with respect to the counter-electrode, all three criteria set forth above are satisfied. It has also been found that if the potential across these copper electrodes is of a magnitude causing the cell to operate in its saturation zone wherein electrical current flowing through the cell is of an intensity that is independent of changes in voltage within the limits of the zone and is proportional to the bulk concentration of chlorine in solution, then the cell will function to analyze chlorine residuals without the need for a buffering agent.

Referring now to FIG. 1, there is shown an analyzer in accordance with the invention, the analyzer comprising a cell, generally designated by numeral 10, a flowmeter 11, a flow-rate valve 12, a thermistor 13, and an output current indicator 14.

Cell 10, which may be formed of a transparent synthetic plastic material which has good mechanical strength and is non-reactive with chlorinated water, includes an inlet pressure 15 into which is continuously fed a sample stream of swimming-pool water. Thermistor 13 is placed in the inlet passage to sense the temperature of the incoming stream. A thermistor is a thermally sensitive resistor which exhibits a relatively large negative temperature coefficient of resistance, so that as the temperature of the stream rises, the resistance of the thermistor falls accordingly.

Inlet passage 15 communicates with an annular passage 16 defined by concentric tubes which incorporate the cell electrodes. Mounted so that its active face is exposed on the surface of the inner tube of annular passage 16, is a disc-shaped measuring electrode 17 formed of copper, and concentric therewith is a copper counter-electrode 18 in annular form, the active face of which is exposed on the surface of the outer tube of annular passage 16. Thus the stream passing through the annular passage 16 makes contact with electrodes 17 and 18.

Annular passage 16 communicates with flowmeter 11, which is of the rotameter type including a tapered metering tube 19 and a float 20, the rotameter being combines with rate valve 12 leading to the fluid outlet 21.

Thus the flow rate of the sample stream may be varied by valve 12 and indicated by the flowmeter 11. In practice, the flow rate may be adjusted to about three-fourths of a liter per minute. It has been found that the reading of the chlorine residual analyzer is stable throughout a range of flow rates, and the same reading will be maintained, for example, in a flow range of ½ to 1 liter per minute.

Electrodes 17 and 18 are connected to current indicator 14 in series with a battery 22 contained in a circuit box 23, the thermistor 13 being shunted across the indicator, as shown in the schematic diagram of FIG. 2. It is to be noted that the polarity of voltage applied to the measuring electrode is negative relative to the voltage on the counter-electrode 18.

FIG. 3 graphically illustrates the relationship which exists between the current output of the cell, whose electrodes of copper, and the direct voltage impressed across the cell, first in the absence of chlorine, and then in the presence of free chlorine with no combined chlorine present, and finally with both free and combined chlorine present.

Curve A shows current flow in microamperes plotted against the voltage on the measuring electrode in a range running from 0.1 volts positive through zero to 0.6 volts negative, in the absence of chlorine residual in any form in the sample stream. It will be seen that almost no current flows until the value of −0.2 volts is reached, at which point the current proceeds to rise with further increases in negative voltage on the measuring electrode.

In the presence of free chlorine at approximately 1 ppm (zero combined chlorine), curve B indicates that for values of voltage extending from +0.1 volts through zero to about −0.13 volts, the current rises sharply until a plateau is reached which is maintained to about −0.4 volts, at which point the current again proceeds to rise with further increases in negative voltage on the measuring electrode.

It is evident from curve B that if the voltage across the cell is increased in the negative direction with respect to the measuring electrode, at some potential more negative than the starting potential, initiation of a steady cathodic current will be observed due to the reduction of chlorine at the measuring electrode but with increasing negative potential, and the current increase levels off at the plateau, which constitutes a saturation voltage zone. The current produced in the saturation voltage zone is called the "limiting current," which results from mass transport of the chlorine from the solution to the measuring electrode surface. At the plateau, the limiting current is proportional to the bulk concentration of the chlorine in solution.

Beyond the saturation voltage zone, the highly negative potential then applied to the measuring electrode gives rise to an increase in current above the limiting current level, by reason of a reduction of the electrolytic water solution.

At the optimum negative voltage value of −0.15 volts, the limiting current in curve B, indicative of 1 ppm free chlorine, lies in the saturation voltage zone and is substantially insensitive to voltage variations within the zone, whereas at the same optimum voltage, no current flows in the absence of chlorine, as indicated by curve A. The limiting current values which are developed at the same optimum voltage for higher bulk concentration of chlorine (2 ppm, 3 ppm, etc.), are proportional thereto. Thus, by maintaining the voltage at an optimum value within the saturation voltage zone, a reading is provided on current indicator 14 which represents the chlorine content in the sample stream. This reading is indicative of the free chlorine residuals, and has been found to be accurate despite pH variations from 5.5 to 9.0.

When combined chlorine is also present, as indicated by curve C, at a point beyond the optimum voltage point, the current rises, but by maintaining the voltage at the optimum point, the instrument remains insensitive to the presence of combined chlorine.

Since the output of cell 10 is also a function of the temperature of the sample water, it is essential to include a temperature-compensating device to automatically correct for the effect of temperature on the reading. This is the function of thermistor 13, which reduces current flowing in the indicator to the extent that it is increased by a rise in temperature.

In a cell of the above-described type, sensitivity of the copper measuring electrode is maintained for many months without the need to add reagents or buffers to the sample stream. Since the current output of the cell is proportional to chlorine content, it may also be applied to a process-control system to automatically regulate the chlorine feed into the swimming pool so as to maintain a desired concentration of chlorine residual herein.

I have found that the use of copper or copper-based materials for both the measuring and counter-electrodes is essential to the instrument. If, for example, gold or other metal is substituted for the copper counter-electrode, then the half-cell potential of the counter-electrode will not be stable and will not act as a reference with respect to the measuring electrode. On the other hand, should gold, platinum or other metal be substituted for the copper of the measuring electrode, the resultant polarization in the presence of free chlorine will cause the output to assume a reduced value in a relatively short time, and the instrument will not be reliable. Consequently, the use of copper for both the measuring and counter-electrodes is of critical importance.

While there has been shown and described a preferred embodiment of an in-line residual chlorine analyzer in accordance with the invention, it will be appreciated that many changes and modifications may be made therein without, however, departing from the essential spirit of the invention. Thus, while the invention has been described in connection with testing swimming-pool water, it is to be understood that it is fully applicable to measuring chlorine residuals in any form of chlorinated water, such as drinking water and water for cooling towers. It may be used, for example, in conjunction with power plants, air-conditioning systems, or in any other systems in which recirculated water has chlorine added thereto as an algacide to prevent the formation of slime.

I claim:

1. The method of testing the free chlorine content of a chlorinated water supply without the use of buffering agents, said method comprising the steps:
   A. deriving a sample stream from the water supply and passing it through the passage between spaced copper measuring and counterelectrodes of an amperometric cell whereby the electrodes make electrical contact with the sample stream;
   B. applying across the electrodes of the cell a direct voltage in a polarity which renders the measuring electrode negative relative to the counterelectrode and with a potential level causing the cell to operate in a saturation voltage zone in which a limiting current flow produced by the presence of free chlorine residual in the stream is substantially proportional to the concentration thereof and is substantially independent of changes in voltage in said zone; and
   C. indicating the intensity of said current to provide a reading of the concentration of free chlorine residual in said supply.

2. The method as set forth in claim 1, further including the steps of regulating the rate of flow of said sample stream through said passage.

3. The method as set forth in claim 1, further including the steps of sensing the temperature of said sample stream and compensating said reading with respect to temperature.

* * * * *

UNITED STATES PATENT OFFICE
CERTIFICATE OF CORRECTION

PATENT NO. : 3,959,087
DATED : May 25, 1976
INVENTOR(S) : James J. Morrow

It is certified that error appears in the above-identified patent and that said Letters Patent are hereby corrected as shown below:

Column 1, line 27 "hydrochlorous" should have read -- hypochlorous --

Column 4, line 57 "pressure" should have read -- passage --

Column 6, line 39 "herein" should have read -- therein --

Signed and Sealed this

Third Day of August 1976

[SEAL]

Attest:

RUTH C. MASON
Attesting Officer

C. MARSHALL DANN
Commissioner of Patents and Trademarks